US010799351B2

(12) United States Patent
Wang et al.

(10) Patent No.: US 10,799,351 B2
(45) Date of Patent: Oct. 13, 2020

(54) RETAINERS FOR TRANSCATHETER HEART VALVE DELIVERY SYSTEMS

(71) Applicant: St. Jude Medical, Cardiology Division, Inc., St. Paul, MN (US)

(72) Inventors: Huisun Wang, Maple Grove, MN (US); Valerie J. Glazier, Eden Prairie, MN (US); Jacob John Daly, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 380 days.

(21) Appl. No.: 15/259,842

(22) Filed: Sep. 8, 2016

(65) Prior Publication Data

US 2016/0374805 A1 Dec. 29, 2016

Related U.S. Application Data

(62) Division of application No. 13/823,337, filed as application No. PCT/US2011/001596 on Sep. 16, 2011, now Pat. No. 9,439,795.

(Continued)

(51) Int. Cl.
*A61F 2/24* (2006.01)
*A61F 2/966* (2013.01)
*A61M 25/06* (2006.01)

(52) U.S. Cl.
CPC .......... *A61F 2/2436* (2013.01); *A61F 2/2418* (2013.01); *A61F 2/966* (2013.01);
(Continued)

(58) Field of Classification Search
CPC .................... A61F 2/966; A61F 2/2436; A61F 2002/9505; A61F 2002/9665;
(Continued)

(56) References Cited

U.S. PATENT DOCUMENTS 4,423,730 A     1/1984   Gabbay
4,471,777 A * 9/1984   McCorkle, Jr. ...... A61B 17/221
                                                                      294/100
(Continued)

FOREIGN PATENT DOCUMENTS

DE    102004062296 A1   7/2006
EP         1129744 A1   9/2001
(Continued)

OTHER PUBLICATIONS

International Search Report and Written Opinion for Application No. PCt/US2011/001218 dated Nov. 11, 2011.
(Continued)

*Primary Examiner* — Tan-Uyen T Ho
*Assistant Examiner* — Charles M Wei
(74) *Attorney, Agent, or Firm* — Lerner, David, Littenberg, Krumholz & Mentlik, LLP

(57) ABSTRACT

A delivery device 10 for a collapsible prosthetic heart valve includes a catheter assembly 16 including a shaft 26 around which a compartment 23 is defined, the compartment 23 being adapted to receive the valve in an assembled condition, and a retainer 30 including a pusher 32 and a holder 34 adapted to retain a stent portion 106 of the valve. The catheter assembly 16 also includes a distal sheath 24 adapted to selectively cover and uncover the compartment 23 and the valve, the distal sheath 24 extending around the shaft 26 at least when the distal sheath 24 covers the compartment 23. The pusher 32 includes one or more recesses 40 in a retention edge 33 thereof, each recess 40 being adapted to receive a junction 107 at an end of the stent portion 106 of the valve. The holder 34 includes one or more elongated ribs 50, each rib 50 being adapted to fit into a cell opening 108 of the stent portion 106 of the valve.

19 Claims, 7 Drawing Sheets

Related U.S. Application Data

(60) Provisional application No. 61/384,014, filed on Sep. 17, 2010.

(52) U.S. Cl.
CPC .............. *A61F 2002/9665* (2013.01); *A61F 2230/0054* (2013.01); *A61M 2025/0681* (2013.01)

(58) Field of Classification Search
CPC ...... A61F 2002/9511; A61F 2002/9583; A61F 2002/9586; A61F 2/2427–2439; A61F 2/2466; A61F 2/95; A61F 2/954; A61F 2/962; A61F 2/97; A61F 2002/0072
See application file for complete search history.

(56) References Cited

U.S. PATENT DOCUMENTS

| | | | |
|---|---|---|---|
| 4,546,759 A | 10/1985 | Solar | |
| 4,575,371 A | 3/1986 | Nordqvist et al. | |
| 5,090,958 A | 2/1992 | Sahota | |
| 5,120,299 A | 6/1992 | Lombardi | |
| 5,201,901 A | 4/1993 | Harada et al. | |
| 5,334,160 A | 8/1994 | Ellis | |
| 5,411,552 A | 5/1995 | Andersen et al. | |
| 5,733,325 A | 3/1998 | Robinson et al. | |
| 5,766,151 A | 6/1998 | Valley et al. | |
| 5,795,325 A | 8/1998 | Valley et al. | |
| 5,797,952 A | 8/1998 | Klein | |
| 5,827,324 A | 10/1998 | Cassell et al. | |
| 5,868,706 A | 2/1999 | Cox | |
| 5,868,755 A | 2/1999 | Kanner et al. | |
| 5,924,424 A | 7/1999 | Stevens et al. | |
| 5,968,068 A | 10/1999 | Dehdashtian et al. | |
| 5,980,533 A * | 11/1999 | Holman | A61F 2/95 606/191 |
| 6,051,014 A | 4/2000 | Jang | |
| 6,077,295 A | 6/2000 | Limon et al. | |
| 6,139,517 A | 10/2000 | Macoviak et al. | |
| 6,146,415 A | 11/2000 | Fitz | |
| 6,190,357 B1 | 2/2001 | Ferrari et al. | |
| 6,214,036 B1 | 4/2001 | Letendre et al. | |
| 6,231,588 B1 | 5/2001 | Zadno-Azizi | |
| 6,306,141 B1 | 10/2001 | Jervis | |
| 6,312,407 B1 | 11/2001 | Zadno-Azizi et al. | |
| 6,361,545 B1 | 3/2002 | Macoviak et al. | |
| 6,375,668 B1 | 4/2002 | Gifford et al. | |
| 6,482,228 B1 | 11/2002 | Norred | |
| 6,592,612 B1 | 7/2003 | Samson et al. | |
| 6,607,551 B1 | 8/2003 | Sullivan et al. | |
| 6,623,518 B2 | 9/2003 | Thompson et al. | |
| 6,673,040 B1 | 1/2004 | Samson et al. | |
| 6,776,791 B1 | 8/2004 | Stallings et al. | |
| 7,235,095 B2 * | 6/2007 | Haverkost | A61F 2/90 606/108 |
| 8,414,644 B2 | 4/2013 | Quadri et al. | |
| 8,608,792 B2 * | 12/2013 | Silveira | A61F 2/07 623/1.11 |
| 8,641,749 B2 * | 2/2014 | Barthold | A61F 2/95 623/1.11 |
| 2002/0120323 A1 * | 8/2002 | Thompson | A61F 2/91 623/1.11 |
| 2003/0014007 A1 | 1/2003 | Eidenschink et al. | |
| 2003/0023265 A1 | 1/2003 | Forber | |
| 2003/0199963 A1 | 10/2003 | Tower et al. | |
| 2004/0087900 A1 | 5/2004 | Thompson et al. | |
| 2004/0093063 A1 | 5/2004 | Wright et al. | |
| 2004/0204749 A1 | 10/2004 | Gunderson | |
| 2004/0236406 A1 | 11/2004 | Gregorich | |
| 2004/0267346 A1 | 12/2004 | Shelso | |
| 2004/0267348 A1 | 12/2004 | Gunderson et al. | |
| 2005/0020974 A1 | 1/2005 | Noriega et al. | |
| 2005/0027345 A1 | 2/2005 | Horan et al. | |
| 2005/0033398 A1 | 2/2005 | Seguin | |
| 2005/0049667 A1 | 3/2005 | Arbefeuille et al. | |
| 2005/0049674 A1 | 3/2005 | Berra et al. | |
| 2005/0065590 A1 | 3/2005 | Shelso | |
| 2005/0090890 A1 | 4/2005 | Wu et al. | |
| 2005/0222662 A1 | 10/2005 | Thompson et al. | |
| 2006/0058865 A1 | 3/2006 | Case et al. | |
| 2006/0100688 A1 | 5/2006 | Jordan et al. | |
| 2006/0106415 A1 | 5/2006 | Gabbay | |
| 2006/0111771 A1 | 5/2006 | Ton et al. | |
| 2006/0142848 A1 | 6/2006 | Gabbay | |
| 2006/0149294 A1 | 7/2006 | Argentine et al. | |
| 2006/0167468 A1 | 7/2006 | Gabbay | |
| 2006/0195184 A1 | 8/2006 | Lane et al. | |
| 2006/0259120 A1 | 11/2006 | Vongphakdy et al. | |
| 2006/0276872 A1 * | 12/2006 | Arbefeuille | A61F 2/07 623/1.11 |
| 2007/0027534 A1 | 2/2007 | Bergheim et al. | |
| 2007/0073391 A1 | 3/2007 | Bourang et al. | |
| 2007/0088431 A1 | 4/2007 | Bourang et al. | |
| 2007/0106364 A1 | 5/2007 | Buzzard et al. | |
| 2007/0112422 A1 | 5/2007 | Dehdashtian | |
| 2007/0129749 A1 | 6/2007 | Thomas | |
| 2007/0142858 A1 | 6/2007 | Bates | |
| 2007/0162100 A1 | 7/2007 | Gabbay | |
| 2007/0168013 A1 | 7/2007 | Douglas | |
| 2007/0203561 A1 | 8/2007 | Forster et al. | |
| 2007/0203575 A1 | 8/2007 | Forster et al. | |
| 2007/0233224 A1 | 10/2007 | Leynov et al. | |
| 2007/0239271 A1 | 10/2007 | Nguyen | |
| 2007/0293930 A1 | 12/2007 | Wang et al. | |
| 2007/0293942 A1 | 12/2007 | Mirzaee | |
| 2008/0103443 A1 | 5/2008 | Kabrick et al. | |
| 2008/0114442 A1 * | 5/2008 | Mitchell | A61F 2/07 623/1.13 |
| 2008/0114443 A1 * | 5/2008 | Mitchell | A61F 2/07 623/1.13 |
| 2008/0140189 A1 * | 6/2008 | Nguyen | A61F 2/2412 623/2.11 |
| 2008/0147182 A1 | 6/2008 | Righini et al. | |
| 2008/0221666 A1 | 9/2008 | Licata et al. | |
| 2008/0228255 A1 | 9/2008 | Rust et al. | |
| 2008/0255662 A1 | 10/2008 | Stacchino et al. | |
| 2008/0262590 A1 | 10/2008 | Murray | |
| 2008/0319526 A1 | 12/2008 | Hill et al. | |
| 2009/0054975 A1 | 2/2009 | del Nido et al. | |
| 2009/0143851 A1 | 6/2009 | Paul, Jr. | |
| 2009/0204197 A1 | 8/2009 | Dorn et al. | |
| 2009/0222035 A1 | 9/2009 | Schneiderman | |
| 2009/0228093 A1 | 9/2009 | Taylor et al. | |
| 2009/0240320 A1 * | 9/2009 | Tuval | A61F 2/2418 623/1.24 |
| 2009/0259306 A1 * | 10/2009 | Rowe | A61F 2/2418 623/2.12 |
| 2009/0276027 A1 | 11/2009 | Glynn | |
| 2009/0281610 A1 | 11/2009 | Parker | |
| 2009/0287290 A1 | 11/2009 | Macaulay et al. | |
| 2010/0070015 A1 | 3/2010 | Schneider et al. | |
| 2010/0131039 A1 | 5/2010 | Chau et al. | |
| 2010/0145438 A1 * | 6/2010 | Barone | A61F 2/2418 623/2.1 |
| 2010/0152834 A1 | 6/2010 | Hennes et al. | |
| 2010/0268315 A1 | 10/2010 | Glynn et al. | |
| 2010/0274187 A1 * | 10/2010 | Argentine | A61F 2/95 604/96.01 |
| 2010/0312325 A1 | 12/2010 | Dorn | |
| 2011/0029065 A1 | 2/2011 | Wood et al. | |
| 2011/0077731 A1 | 3/2011 | Lee et al. | |
| 2011/0078350 A1 | 3/2011 | Carls | |
| 2011/0098805 A1 | 4/2011 | Dwork et al. | |
| 2011/0137401 A1 | 6/2011 | Dorn et al. | |
| 2011/0137402 A1 | 6/2011 | Dorn et al. | |
| 2011/0172764 A1 | 7/2011 | Badhwar | |
| 2011/0224678 A1 | 9/2011 | Gabbay | |
| 2011/0251665 A1 | 10/2011 | Schmitt et al. | |
| 2011/0251666 A1 | 10/2011 | Schmitt et al. | |
| 2011/0251679 A1 | 10/2011 | Wiemeyer et al. | |
| 2011/0257720 A1 * | 10/2011 | Peterson | A61F 2/95 623/1.11 |

(56) References Cited

U.S. PATENT DOCUMENTS

| | | |
|---|---|---|
| 2011/0264201 A1 | 10/2011 | Yeung et al. |
| 2011/0264202 A1 | 10/2011 | Murray, III et al. |
| 2011/0288636 A1 | 11/2011 | Rolando et al. |
| 2011/0301685 A1* | 12/2011 | Kao .................. A61F 2/95 623/1.11 |
| 2012/0078350 A1 | 3/2012 | Wang et al. |
| 2012/0123528 A1 | 5/2012 | Knippel et al. |
| 2012/0179033 A1 | 7/2012 | Merhi |
| 2013/0116654 A1 | 5/2013 | Dehdashtian et al. |
| 2013/0131775 A1 | 5/2013 | Hadley et al. |
| 2013/0204344 A1 | 8/2013 | Tatalovich et al. |
| 2013/0274860 A1 | 10/2013 | Argentine |
| 2014/0005768 A1 | 1/2014 | Thomas et al. |

FOREIGN PATENT DOCUMENTS

| | | |
|---|---|---|
| EP | 1157673 A2 | 11/2001 |
| WO | 9620025 A1 | 7/1996 |
| WO | 9748343 A1 | 12/1997 |
| WO | 990065418 A1 | 12/1999 |
| WO | 2006069704 A2 | 7/2006 |
| WO | 2006124549 A1 | 11/2006 |
| WO | 2007002863 A2 | 1/2007 |
| WO | 2007134290 A2 | 11/2007 |
| WO | 2008031103 A2 | 3/2008 |
| WO | 2008097556 A1 | 8/2008 |
| WO | 2009062955 A1 | 5/2009 |
| WO | 2009091509 A1 | 7/2009 |
| WO | 2009108942 A1 | 9/2009 |
| WO | 2010005524 A2 | 1/2010 |
| WO | 2010022138 A2 | 2/2010 |
| WO | 10051025 A1 | 5/2010 |
| WO | 10087975 A1 | 8/2010 |
| WO | 2011025945 A1 | 3/2011 |
| WO | 2012009006 A1 | 1/2012 |
| WO | 2012036740 A2 | 3/2012 |
| WO | 2012038550 A1 | 3/2012 |

OTHER PUBLICATIONS

International Search Report and Written Opinion for Application No. PCT/US2012/047283 dated Oct. 30, 2012.

International Search Report and Written Opinion for Application No. PCT/US2013/047891 dated Dec. 4, 2013.

International Search Report and Written Opinion for Application No. PCT/US2013/048413 dated Dec. 4, 2013.

International Search Report dated Feb. 2, 2012 for Application No. PCT/US2011/001446.

International Search Report for Application No. PCT/US2011/001596 dated May 8, 2012.

Japanese Office Action for Application No. 2013-519648 dated Jun. 30, 2015.

* cited by examiner

FIG. 8
FIG. 9
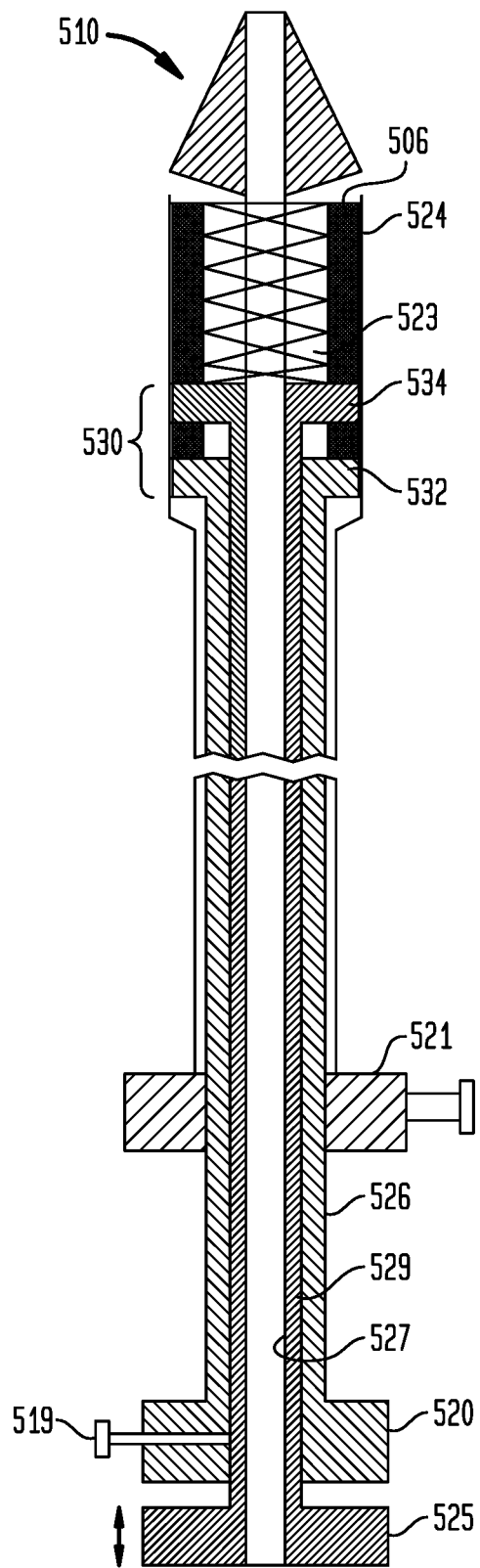
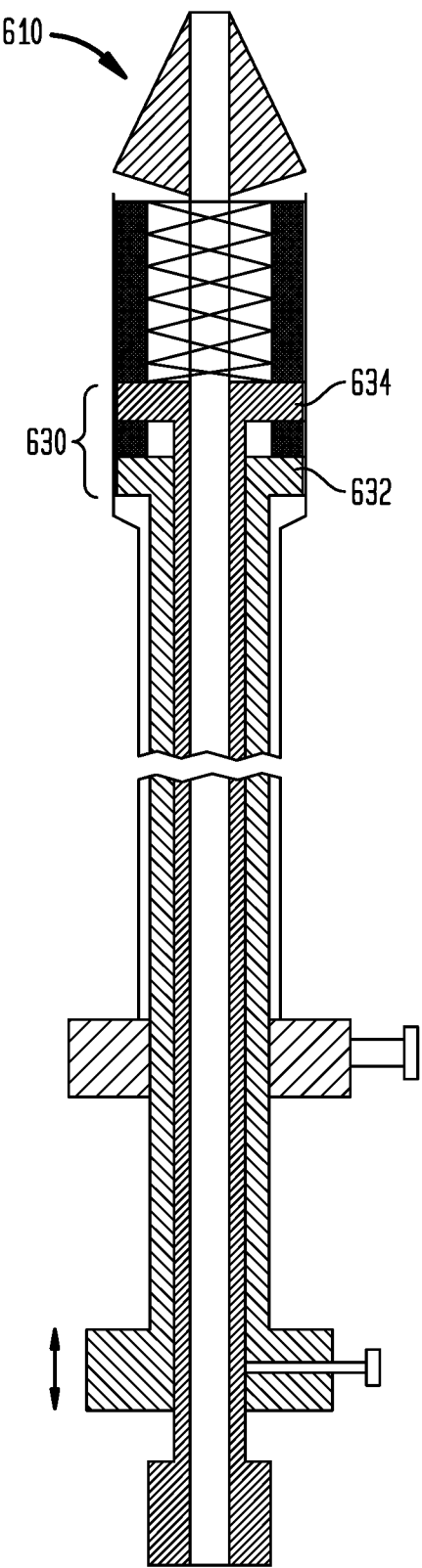

RETAINERS FOR TRANSCATHETER HEART VALVE DELIVERY SYSTEMS

CROSS-REFERENCE TO RELATED APPLICATIONS

This application is a divisional of U.S. application Ser. No. 13/823,337, filed on Jul. 10, 2013, which is a national phase entry under 35 U.S.C. §371 of International Application No. PCT/US2011/001596 filed on Sep. 16, 2011, published in English, which claims the benefit of U.S. Provisional Patent Application No. 61/384,014, filed on Sep. 17, 2010, the disclosures of which are hereby incorporated herein by reference.

BACKGROUND OF THE INVENTION

The present invention is related to prosthetic heart valve replacement, and more particularly to devices, systems, and methods for transcatheter delivery of collapsible prosthetic heart valves for deployment in a patient.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valves structures are ordinarily mounted: self-expanding stents and balloon-expandable stents. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and expanded to full operating size. For balloon-expandable valves, this generally involves releasing the entire valve, assuring its proper location, and then expanding a balloon positioned within the valve stent. For self-expanding valves, on the other hand, the stent automatically begins to expand as the sheath covering the valve is withdrawn.

In conventional delivery systems for self-expanding aortic valves, after the delivery system has been positioned for deployment, the annulus end of the valve is typically unsheathed and expanded into engagement with the valve annulus, while the aortic end of the valve remains sheathed. Once the annulus end of the valve has expanded, it may be determined that the valve needs to be repositioned in the patient's valve annulus. To accomplish this, a user (such as a surgeon or an interventional cardiologist) typically resheathes the annulus end of the valve, so that the valve can be repositioned while in a collapsed state. After the valve has been repositioned, the user can again unsheathe the valve for deployment.

Once a self-expanding valve has been fully deployed, it expands to a diameter larger than that of the sheath that previously retained the valve in the collapsed condition, making resheathing impossible, or difficult at best. In order for a user to be able to resheathe a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings For example, in conventional delivery devices for self-expanding valves, the valve may be held in a compartment of the device by the engagement of retention members on the stent with one or more retainers in the compartment. During deployment of the valve into the desired area (e.g., the valve annulus), the high frictional force produced during unsheathing of the valve may cause high axial forces to be applied directly to the stent retention members, which may damage or deform the stent struts that support the retention members.

There therefore is a need for further improvements to the devices, systems, and methods for transcatheter delivery of collapsible prosthetic heart valves. Among other advantages, the present invention may address one or more of these needs.

BRIEF SUMMARY OF THE INVENTION

Delivery devices for a collapsible prosthetic heart valve and a method of delivering a collapsible prosthetic heart valve are disclosed.

A delivery device for a collapsible prosthetic heart valve includes a catheter assembly including a principal shaft around which a compartment is defined, the compartment being adapted to receive the valve in an assembled condition, the catheter assembly further including a distal sheath adapted to selectively cover and uncover the compartment and the valve, the distal sheath extending around the principal shaft at least when the distal sheath covers the compartment, and a retainer, including a pusher having at least one recess in a retention edge thereof, the recess being adapted to receive a junction at an end of a stent portion of the valve, and a holder having at least one elongated rib adapted to fit into a cell opening in the stent portion of the valve.

The pusher may be slidable relative to the holder along a longitudinal axis of the delivery device. The holder may be slidable relative to the pusher along a longitudinal axis of the delivery device. The at least one recess may be shaped to substantially match the shape of outward-facing surfaces of the junction. The at least one rib may have a width in a circumferential direction, an end of the rib relatively close to the pusher may have a first width and an end of the rib relatively far from the pusher may have a second width greater than the first width, such that the rib may be shaped to substantially match the shape of inward-facing surfaces of the cell opening contacted by the rib. The at least one rib may have a cross-sectional shape in a circumferential direction that includes an undercut. The at least one recess may have a cross-sectional shape in a circumferential direction that includes an undercut.

The at least one recess may be a continuous annular channel formed in the retention edge of the pusher adjacent a circumference of the pusher. The principal shaft may be affixed to the holder, and the delivery device may also include a pusher shaft affixed to the pusher and extending along a longitudinal axis of the delivery device outside of the principal shaft. The delivery deice may also include a locking pin adapted to temporarily affix the principal shaft to the pusher shaft so that the distal sheath may be slidable along the longitudinal axis relative to the affixed principal shaft and pusher shaft. The principal shaft may be affixed to the holder, and the delivery device may also include a pusher shaft affixed to the pusher and extending along a longitudinal axis of the delivery device inside of the principal shaft. The delivery deice may also include a locking pin adapted to temporarily affix the principal shaft to the pusher shaft so that the distal sheath may be slidable along the longitudinal axis relative to the affixed principal shaft and pusher shaft.

A delivery device for a collapsible prosthetic heart valve includes a catheter assembly including a principal shaft around which a compartment is defined, the compartment being adapted to receive the valve in an assembled condition, the catheter assembly further including a distal sheath adapted to selectively cover and uncover the compartment and the valve, the distal sheath extending around the principal shaft at least when the distal sheath covers the compartment, and a retainer, including a retention portion affixed to the principal shaft and including a plurality of acceptances adapted to receive retention members extending from an end of a stent portion of the valve, and a spacer portion having a plurality of circumferentially spaced elongated ribs, each adjacent pair of ribs defining a channel therebetween, each channel being adapted to receive a junction at the end of the stent portion of the valve.

A method of delivering a collapsible prosthetic heart valve includes providing a delivery device including a principal shaft around which a compartment is defined, a distal sheath adapted to selectively cover and uncover the compartment, the distal sheath extending around the principal shaft at least when the distal sheath covers the compartment, and a retainer including a pusher and a holder, the pusher having at least one recess in a retention edge thereof and the holder having at least one elongated rib, mounting in the compartment a collapsible prosthetic heart valve having a stent portion including a plurality of junctions at an end thereof and a plurality of cell openings defined therein, the valve being mounted so that at least one of the junctions is positioned in the at least one recess and the at least one rib is positioned in at least one of the cell openings, moving the distal sheath to cover the compartment and the valve, inserting the delivery device in a patient to position the valve at a target location, and deploying the valve by moving the distal sheath to uncover the compartment and the valve.

The method may also include sliding at least one of the pusher and the holder towards another of the pusher and the holder, thereby capturing the junctions positioned therebetween. The principal shaft may be affixed to the holder, the pusher may be affixed to a pusher shaft, and the sliding step may include sliding at least one of the principal shaft and the pusher shaft relative to another of the principal shaft and the holder shaft. The method may also include, after the sliding step, temporarily fixing the position of the pusher relative to the holder. The method may also include, after the inserting step, releasing at least one of the pusher and the holder for movement relative to one another. The method may also include sliding at least one of the pusher and the holder away from another of the pusher and the holder, thereby releasing the junctions positioned therebetween.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

FIG. 8 is a longitudinal cross-section of another embodiment of a transfemoral delivery device for a collapsible prosthetic heart valve having a slidable holder portion;

FIG. 9 is a longitudinal cross-section of a further embodiment of a transfemoral delivery device for a collapsible prosthetic heart valve having a slidable pusher portion;

DETAILED DESCRIPTION

As used herein, the terms "proximal" and "distal" are to be taken as relative to a user (e.g., a surgeon or an interventional cardiologist) using the disclosed delivery devices. "Proximal" is to be understood as relatively close to the user and "distal" is to be understood as relatively farther away from the user.

Figure 1:
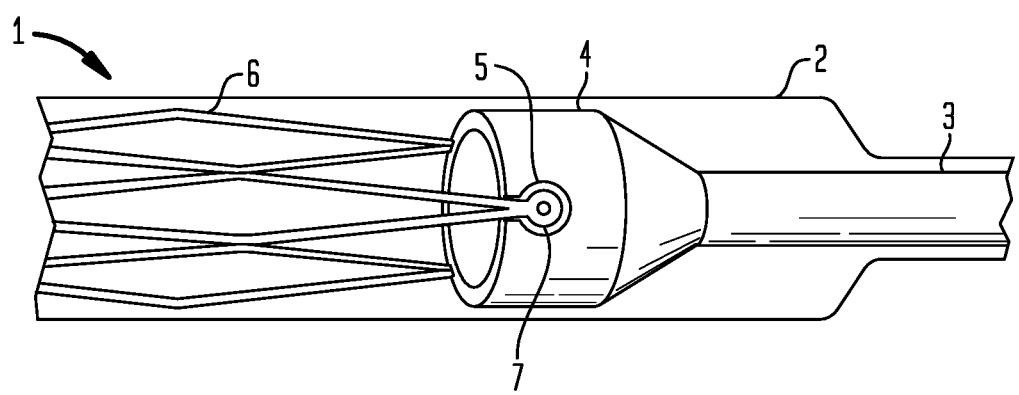
FIG. 1 is a side view of a conventional transfemoral delivery device for a collapsible prosthetic heart valve.

Referring to FIG. 1, an exemplary prior art transfemoral delivery device 1 for a collapsible prosthetic heart valve has a distal sheath 2 surrounding and slidably coupled to an inner shaft 3. The inner shaft 3 is attached to a retainer 4 having a plurality of acceptances 5. The acceptances 5 are adapted to receive a plurality of retention members 7 on the stent portion 6 of a collapsible prosthetic heart valve to thereby couple the valve to the retainer 4.

The acceptances 5 hold the retention members 7 during unsheathing of the valve, as friction forces between the valve and the distal sheath 2 act to pull the retention members against the closed end of the acceptances 5. The acceptances 5 also hold the retention members 7 during resheathing of the valve, as friction forces between the valve and the distal sheath 2 act to push the retention members against a constricted open neck of the acceptances 5. The pushing and pulling on the retention members 7 during unsheathing and resheathing of the valve may damage or deform the stent struts that support the retention members.

Figure 2A:
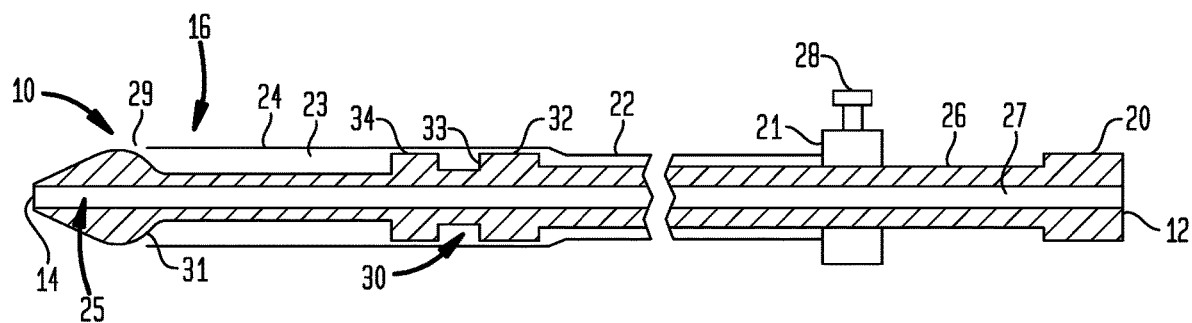
FIG. 2A is a longitudinal cross-section of one embodiment of a transfemoral delivery device for a collapsible prosthetic heart valve in accordance with the present invention.
Figure 2B:
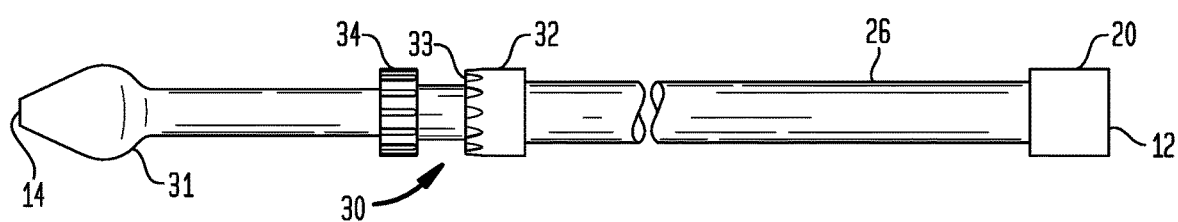
FIG. 2B is a side elevation of the inner shaft and retainer of the delivery device shown in FIG. 2A.
Figure 2C:
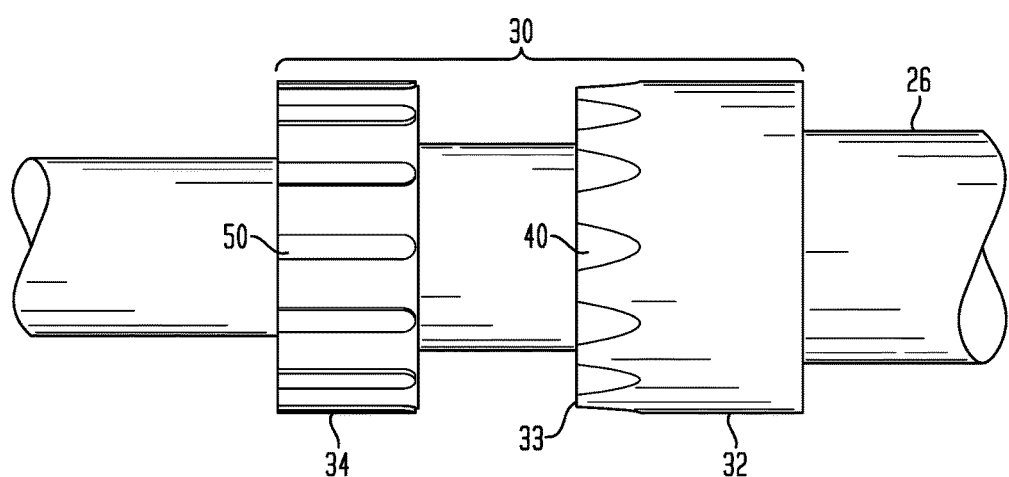
FIG. 2C is an enlarged side elevation of the retainer shown in FIG. 2B.

Referring now to FIGS. 2A-2C to illustrate the structure and function of the present invention, an exemplary transfemoral delivery device 10 for a collapsible prosthetic heart valve includes a catheter assembly 16 for delivering the heart valve to and deploying the heart valve at a target location. The delivery device 10 extends from a proximal end 12 to a distal end 14. The catheter assembly 16 is adapted to receive a collapsible prosthetic heart valve in an assembled condition in a compartment 23 defined around an inner shaft 26 between a retainer 30 affixed to the inner shaft and the proximal end of an atraumatic tip 31. The inner shaft 26 extends from a hub 20 to the atraumatic tip 31, and includes a central lumen 27 adapted to receive a guide wire therethrough. The guide wire may exit the distal end 14 of the delivery device 10 through a central bore 25 in the tip 31, which is axially aligned with the lumen 27.

A distal sheath 24 surrounds the compartment 23 and is slidable relative to the inner shaft 26 such that it can selectively cover or uncover a collapsed prosthetic heart valve positioned in the compartment. An outer shaft 22 is connected at one end to the proximal end of the distal sheath 24 and at its other end to a hub 21. The distal end 29 of the distal sheath 24 abuts a conical surface of the tip 31 when the distal sheath fully covers the compartment 23, and is spaced apart from the tip 31 when the compartment 23 is at least partially uncovered. A hemostasis valve 28 (shown, for example, in FIG. 2A) has an internal gasket adapted to create a seal between the inner shaft 26 and the proximal end of the outer shaft 22. The hubs 20 and 21 optionally may be affixed to an operating handle (not shown) adapted to allow a user to selectively slide the outer shaft 22 relative to the inner shaft 26 and to provide a mechanical advantage to the user to help overcome the friction forces acting on the outer shaft and the distal sheath 24 during their motion relative to the inner shaft.

The retainer 30 includes a pusher 32 located at the proximal end of the retainer and a holder 34 located at the distal end of the retainer. The pusher 32 and the holder 34 are affixed to the inner shaft 26 so that they remain stationery as the distal sheath 24 is moved proximally or distally relative to compartment 23. The pusher 32 and the holder 34 may be formed integrally with the inner shaft 26 or may be formed separately and affixed to the inner shaft by adhesive, welding or any other known joining technique.

The pusher 32 includes a plurality of recesses 40 which extend proximally from a distal retention edge 33 thereof. The recesses 40 may be spaced substantially equally about the outside circumferential surface of the pusher 32 and are configured to receive respective V-shaped junctions formed by the struts at the end of the stent portion of a prosthetic valve (V-shaped strut junctions are shown engaged in similar recesses in FIG. 3A).

The holder 34 includes one or more ribs 50 projecting radially outward from the outside circumferential surface of the holder. The ribs 50 are oriented in the longitudinal direction of the inner shaft 26 and may be spaced substantially equally apart such that each rib is aligned in the longitudinal direction with a recess 40 in the pusher 32. Each recess 50 is adapted to be received in a diamond-shaped cell opening located adjacent to the V-shaped junction formed by the struts at the end of the stent portion of a prosthetic valve (exemplary diamond shaped cell openings are shown engaged by similar ribs in FIG. 3A).

In contrast to the prior art delivery device 1, the delivery device 10 is adapted to deliver a prosthetic valve having a stent portion that does not have retention members extending therefrom (e.g., the retention members 7 shown in FIG. 1). Rather, a valve is retained in the delivery device 10 by engagement of the stent portion of the valve with the recesses 40 of the pusher 32 and the ribs 50 of the holder 34. During deployment of the valve, the pusher 32 is adapted to push distally on the V-shaped junctions of the stent portion of the valve to restrict proximal movement of the valve resulting from the friction force acting between the valve and the distal sheath 24 as the distal sheath is withdrawn. During resheathing of the valve, the engagement of the ribs 50 of the holder 34 in the diamond-shaped cell openings of the stent portion of the valve keeps the valve assembled to the retainer 30. That is, the ribs 50 apply a retention force in a proximal direction to restrict distal movement of the valve resulting from the friction force acting between the valve and the distal sheath 24 as the distal sheath is advanced.

When a prosthetic valve is assembled in the compartment 23 with the distal sheath 24 covering the compartment, the recesses 40 and the ribs 50 are adapted to substantially limit the movement of the valve longitudinally and rotationally relative to the retainer 30, for example, during insertion of the delivery device into a patient. The recesses 40 can provide a limit to longitudinal movement of the valve in a proximal direction, and can substantially fix the circumferential positions of the stent struts, preventing them from overlapping with one another and becoming otherwise entangled during the delivery of the valve to a target location in the patient. The ribs 50 can substantially limit longitudinal movement of the valve in a distal direction, and can also substantially fix the circumferential positions of the stent struts.

To load the delivery device 10 with a collapsible prosthetic valve, a user may retract the distal sheath 24 to expose the compartment 23, collapse the valve around the inner shaft 26, and couple the proximal end of the stent portion of the valve to the pusher 32 and the holder 34 of the retainer 30. To couple the stent portion of the valve to the retainer 30, a user inserts each V-shaped junction formed by the struts at the proximal end of the stent portion of the valve into a corresponding recess 40 of the pusher 32, and aligns the valve such that each rib 50 of the holder 34 is inserted into a corresponding diamond-shaped cell opening located adjacent to the V-shaped junctions. The user may then slide the distal sheath 24 over the compartment 23, which holds the valve in a compressed state.

When the valve is in the assembled condition in the compartment 23, the end of the stent portion opposite the end at which the valve structure is located preferably is attached to the retainer 30 (or any of the retainer embodiments disclosed herein), such that the end of the valve that is to be deployed first (e.g., the annulus end of the valve) is located near the atraumatic tip 31.

To use the delivery device 10 to deploy a prosthetic valve that has been compressed and inserted in the compartment 23 and covered by the distal sheath 24, the user may slide the outer shaft 22 and the attached distal sheath proximally relative to the inner shaft 26 to retract the distal sheath from the compartment 23. When the distal sheath 24 has been only partially retracted, the compartment 23 will not be fully exposed and the valve will not be fully deployed. Rather, the proximal end of the valve will still be engaged with the pusher 32 and the holder 34 of the retainer 30 and covered by the distal sheath 24. In this condition, the valve may be resheathed if desired, such as for repositioning the valve relative to the native valve annulus. Resheathing may be accomplished by sliding the distal sheath 24 back over the portion of the stent that has expanded, thereby recollapsing same into the compartment 23.

When the distal sheath 24 is fully retracted from the compartment 23, the valve will be fully unsheathed, and the proximal end of the stent portion of the valve will self-expand and become disengaged from the pusher 32 and the holder 34 of the retainer 30. Disengagement of the stent portion of the valve from the retainer 30 will thus release the valve from the catheter assembly 16.

In a variant of the delivery device 10, the recesses 40 may be omitted from the pusher 32. In such an embodiment, the retention edge 33 of the pusher 32 may push distally on the V-shaped junctions of the stent portion of the valve during deployment of the valve into a patient.

Figure 3A:
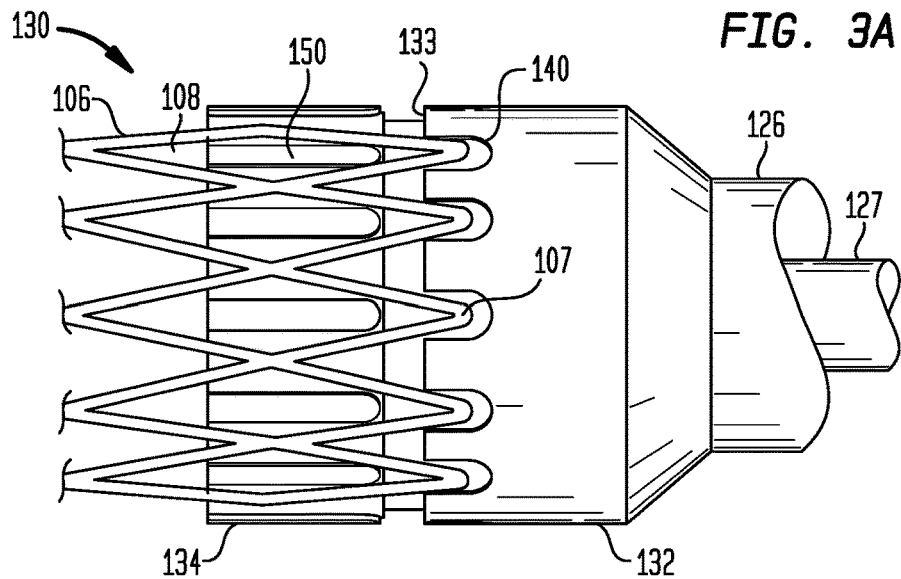
FIG. 3A is an enlarged side elevation of another embodiment of a retainer suitable for use in the delivery device of FIG. 2A, showing the stent portion of a valve assembled thereto.
Figure 3B:
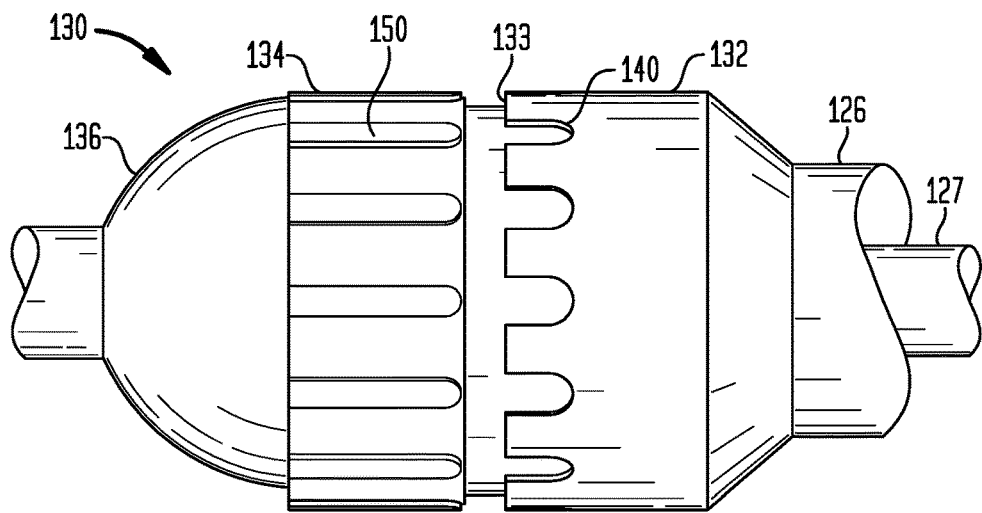
FIG. 3B is an enlarged side elevation of the retainer of FIG. 3A, showing a retainer cone but not the stent portion of the valve.

FIGS. 3A and 3B show a retainer 130 in accordance with another embodiment of the invention, which is suitable for use with the catheter assembly 16 described above. The retainer 130 is similar to the retainer 30 described above, except that the pusher 132 and the holder 134 are spaced closer together, the transition between the pusher 132 and the inner shaft 126 includes a gradual slant rather than an abrupt change in diameter, and the holder 134 includes a distal conical end 136. Furthermore, FIG. 3A shows a stent portion 106 of a collapsible prosthetic heart valve engaged with the retainer 130.

As described above with reference to FIGS. 2A-2C, the stent portion 106 of the valve includes V-shaped junctions 107 formed by the struts at one end thereof that engage with the recesses 140 in the pusher 132. Each recess 140 may be slightly wider in the circumferential direction than the compressed width of a corresponding junction 107 when the stent portion 106 is in an assembled condition. However, the uncompressed width of a junction 107 may be slightly wider in the circumferential direction than a corresponding recess 140, such that the junction is slightly compressed in the circumferential direction when inserted into a recess.

Each recess 140 may have a U-shaped profile that approximately matches the V-shape of a corresponding junction 107, such that the junction contacts the pusher 132 at the closed end of the recess and at each side at the open end of the recess. Alternatively, each recess 140 may closely match the shape of the corresponding junction 107, such that the contact between each recess and junction occurs over a greater portion of the junction 107 and the recess than is shown in FIG. 3A.

The stent portion 106 of the valve also includes diamond-shaped cell openings 108 located adjacent to the V-shaped junctions 107 that engage with the ribs 150 of the holder 134. Each rib 150 may be slightly narrower in the circumferential direction than the maximum width near the center of a corresponding diamond-shaped cell opening 108 when the stent portion 106 is in the assembled condition. However, the width at the longitudinal ends of a cell opening 108 may be slightly narrower in the circumferential direction than the width of a corresponding rib 150, such that the ribs tend to expand the cell openings 108 in the circumferential direction at the points at which the ribs contact the stent portion 106. As shown in FIG. 3A, each rib 150 may have straight lateral edges that are substantially parallel to the longitudinal axis of the retainer 130, such that each rib contacts the stent portion 106 near a junction 107, thereby limiting the distal movement of the stent portion 106 relative to the retainer.

Figure 4:
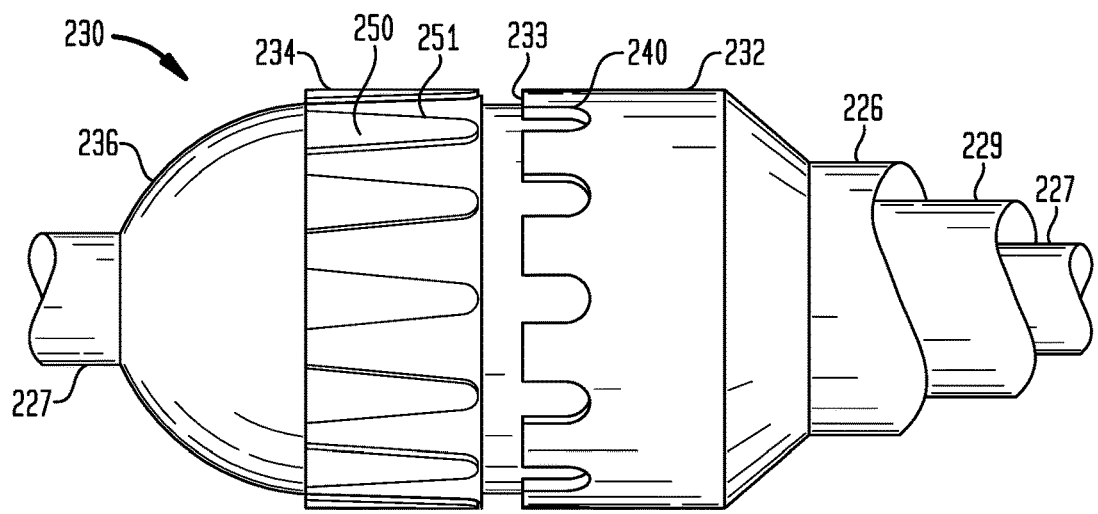
FIG. 4 is an enlarged side elevation of an embodiment of a retainer with a slidable portion suitable for use in the delivery device of FIG. 2A.

Referring now to FIG. 4, a retainer 230 in accordance with another embodiment of the invention is shown. The retainer 230 is suitable for use with the catheter assembly 16 described above with reference to FIG. 2A. The retainer 230 is similar to the retainer 130 described above with reference to FIGS. 3A and 3B, except that the shape of the ribs 250 is more closely matched to the corresponding diamond-shaped cell openings in the stent portion of a collapsible prosthetic heart valve, and the pusher 232 and/or the holder 234 are longitudinally slidable relative to one another.

The holder 234 includes ribs 250 that have lateral edges 251 that are angled relative to the longitudinal axis of the retainer 230, such that the angle formed by the lateral edges 251 of a rib 250 approximately matches the angle formed by the struts of a corresponding junction. Accordingly, each rib 250 is narrower at its proximal end than at its distal end, such that each rib contacts the stent portion of a collapsible prosthetic heart valve along a longer portion of a respective diamond-shaped cell opening than the ribs 150 of the retainer 130.

The pusher 232, the holder 234 or both may be longitudinally slidable so that they may be moved closer to one another or further apart. For a user to control the relative longitudinal sliding of the pusher 232 and the holder 234, the pusher may be fixedly connected to an inner shaft 226 that extends to the proximal end of the delivery device, and the holder may be fixedly connected to a holder shaft 229 that also extends to the proximal end of the delivery device. The holder shaft 229 may be disposed within the inner shaft 226 for sliding movement relative to same. The inner shaft 226 and the holder shaft 229 may be affixed at their proximal ends to respective hubs and/or to an operating handle that allows the user to slide the inner shaft and the holder shaft relative to one another. A central shaft 227 may provide a fixed connection between the distal tip of the delivery device and the holder shaft 229. The central shaft 227 may extend from the distal tip of the delivery device proximally to a location within the holder shaft 229 adjacent the retainer 230, or may extend all the way to the proximal end of the delivery device. The central shaft 227 may have a lumen for a guide wire (not shown) therethrough.

To load a collapsible prosthetic valve into the valve compartment of a delivery device incorporating the retainer 230, a user may engage the stent portion of the collapsed valve into the pusher 232 and the holder 234 by inserting the V-shaped junctions into the recesses 240 and assembling the diamond-shaped cell openings around the ribs 250. The user may then pinch or lock the V-shaped junctions between the recesses 240 and the ribs 250 by sliding the holder 234 and/or the pusher 232 towards one another. Subsequently, the distal sheath may be slid over the compartment to hold the valve in the compressed state.

To deploy the valve, the distal sheath may be slid proximally to gradually uncover the collapsed valve held in the compartment of the delivery device. As portions of the valve are exposed, they will begin to expand radially. Typically, the annulus end of the valve is exposed first. After expansion of the annulus end of the valve (i.e., partial deployment of the valve), it may be desired to reposition the valve in the patient's aortic annulus. However, for the user to be able to resheathe a partially-deployed valve, a portion of the valve must remain collapsed inside of the distal sheath. When using delivery devices that do not have a pusher and a holder that are moveable relative to one another to retain the valve, the user may accidentally fully deploy the valve before the annulus end of the valve is properly located in the patient's aortic annulus. With delivery devices incorporating the retainer 230, however, the user may pull the holder shaft 229 proximately relative to the inner shaft 226, thereby squeezing the stent portion of the valve between the pusher 232 and the holder 234. This squeezing action may keep the valve assembled to the retainer 230 and prevent the accidental full deployment of the valve as the distal sheath is withdrawn. As such, the use of retainer 230 may allow the opportunity to resheathe and reposition the valve prior to full deployment.

To release the valve into the desired position in the patient (i.e., fully deploy the valve), the user may slide the holder shaft 229 distally relative to the inner shaft 226 to separate the holder 234 from the pusher 232. As the holder 234 and the pusher 232 move apart, the valve is released and can self expand when the distal sheath is fully withdrawn from covering the compartment.

Figure 5:
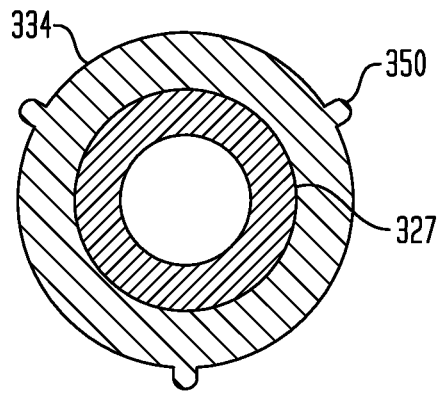
FIG. 5 is a lateral cross-section of a holder portion of a retainer suitable for use in the delivery device of FIG. 2A.

Referring now to FIG. 5, a cross-section of an exemplary embodiment of a holder 334 of a retainer according to the invention is shown. The holder 334 is similar to the holders 34, 134, and 234 described above, except that the holder 334 only includes three ribs 350. The holder 334 is adapted to fit into some of the diamond-shaped cell openings of the stent portion of a prosthetic valve, while circumferentially adjacent cell openings remain empty. For example, when the stent portion of a prosthetic valve having twelve diamond-shaped cell openings spaced about the circumference of the valve is loaded onto the holder 334, only every fourth cell opening is engaged with a rib 350, while the remaining cell openings remain empty. Although the holder 334 is shown with three ribs 350, it may have any number of ribs, including, for example, 2, 4, 6, 8, 9, 10, 12, or 16 ribs, depending on the number of cell openings around the circumference of the valve.

Figure 6A:
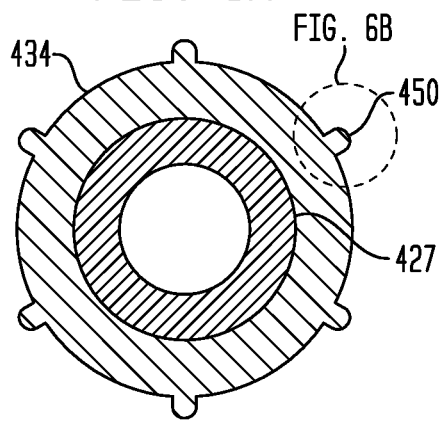
FIG. 6A is a lateral cross-section of another holder portion of a retainer suitable for use in the delivery device of FIG. 2A.

Referring now to FIG. 6A, a cross-section of another exemplary embodiment of a holder 434 of a retainer according to the invention is shown. The holder 434 is similar to the holder 334 described above, except that the holder 434 includes six ribs 450, such that when the stent portion of a valve having twelve diamond-shaped cell openings spaced about the circumference of the valve is mounted onto the holder, only every other cell opening is engaged with a rib, while the other cell openings remain empty.

Figure 6B:
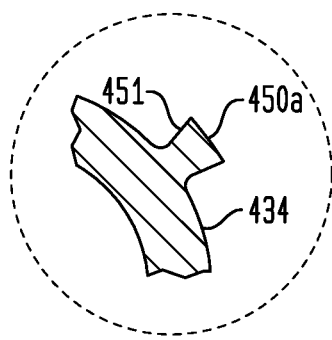
FIG. 6B is a detailed view in cross-section showing a rib of the holder portion of FIG. 6A.

Referring now to FIG. 6B, an enlarged cross-section of an exemplary embodiment of a rib 450a is shown. The rib 450a is similar to the rib 450 shown in FIG. 6A, except that the rib has a cross-sectional shape that includes an undercut, such that each lateral edge 451 that extends generally in the longitudinal direction of the retainer projects outward from the outer surface of the holder 434 at an angle of less than 90°. Having the ribs 450a include such an undercut may increase the ability of the ribs to grip onto the struts of the stent portion of the valve, such that when the holder and a pusher are moved towards one another to lock the valve into the retainer, there may be interference between the struts and the ribs to help prevent the stent portion from sliding off of the ribs, thereby helping to prevent premature deployment of the valve while the holder and pusher are positioned closely together.

Any portion of the longitudinal length of the rib 450a may be undercut, and the remainder of the length of the rib may not be undercut (i.e., a non-undercut portion of the lateral edge 451 projects outward from the outer surface of the holder 434 at an angle of at least 90°). For example, each rib 450a may have undercut lateral edges 451 only at the most proximal 10-20% of the longitudinal length of the rib. In retainer embodiments having ribs including substantially longitudinally oriented lateral edges, such as the ribs shown in FIGS. 2B, 2C, 3A, and 3B, only the most proximal 10-20% of the longitudinal length of the rib may be in contact with the struts of the stent portion of the valve when the valve is engaged with the retainer, so that may be the only portion of the rib at which an undercut may enhance the stent-gripping ability of the rib.

Figure 7A:
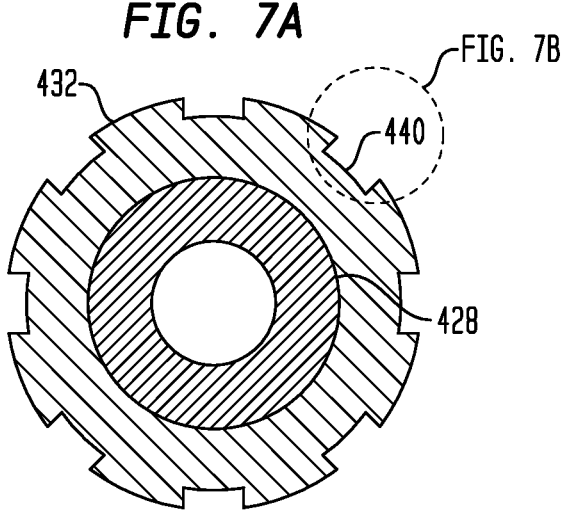
FIG. 7A is a lateral cross-section of a pusher portion of a retainer suitable for use in the delivery device of FIG. 2A.

A cross-section of an exemplary embodiment of a pusher 432 of a retainer according to the invention is shown in FIG. 7A. The pusher 432 is similar to the pushers 32, 132, and 232 described above, except that the pusher 432 includes eight recesses 440. It will be appreciated, however, that the pusher 432 may include any number of recesses, including, for example, 2, 4, 6, 8, 9, 10, 12, or 16 recesses, depending on the number of V-shaped junctions formed at the end of the stent portion of the valve.

Figure 7B:
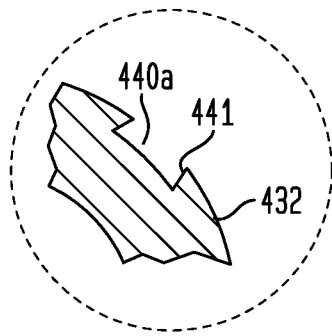
FIG. 7B is a detailed view in cross-section showing a recess of the pusher portion of FIG. 7A.

Referring now to FIG. 7B, an enlarged cross-section of an exemplary embodiment of a recess 440a is shown. The recess 440a is similar to the recess 440 shown in FIG. 7A, except that the recess has a cross-sectional shape that includes an undercut, such that each lateral edge 441 that extends generally in the longitudinal direction of the retainer projects inward from the outer surface of the pusher 432 at an angle of less than 90°. Having the recesses 440a include such an undercut may increase the ability of the recesses to grip onto the V-shaped junctions of the stent portion of the valve, such that when the pusher and a holder are moved towards one another to lock the valve into the retainer, there may be interference between the V-shaped junctions and the recesses to help prevent the stent portion from sliding out from the recesses, thereby helping to prevent premature deployment of the valve while the holder and pusher are positioned closely together.

Any portion of the longitudinal length of the recess 440a be undercut, and the remainder of the length of the recess may not be undercut (i.e., a non-undercut portion of the lateral edge 441 projects inward from the outer surface of the pusher 432 at an angle of at least 90°). For example, each recess 440a may have undercut lateral edges 441 only at the most distal 10-20% of the longitudinal length of the recess. In retainer embodiments having recesses including substantially longitudinally oriented lateral edges, such as the recesses shown in FIGS. 3A, 3B, and 4, only the closed end and the most distal 10-20% of the longitudinal length of the recess may be in contact with the V-shaped junctions of the stent portion of the valve when the valve is engaged with the retainer, so these may be the only portions of the recess at which an undercut may enhance the stent-gripping ability of the recess.

Referring now to FIG. 8, an exemplary transfemoral delivery device 510 for a collapsible prosthetic heart valve according to the invention is shown. The delivery device 510 is similar to the delivery device 10 described above, but includes a retainer similar to the retainer 230 in which the pusher and holder are slidable relative to one another.

The retainer 530 of the delivery device 510 includes a pusher 532 affixed to an inner shaft 526 having a hub 520 on its proximal end. The holder 534 of the retainer 530 is affixed to a holder shaft 529 that extends through the lumen of the inner shaft 526 to a proximal hub 525. In the embodiment shown in FIG. 8, the holder 534 is longitudinally slidable relative to the pusher 532 to capture the proximal end of the stent portion of the valve therebetween, and thereby assemble it to the retainer 530. Although the recesses in the pusher 532 and the ribs in the holder 534 are not shown in FIG. 8, the pusher and the holder may have any of the recess and rib configurations disclosed herein.

The delivery device 510 includes a distal sheath 524 surrounding a compartment 523 adapted to receive a collapsible prosthetic heart valve 506 in an assembled condition around a central shaft 527 that may extend between a distal end of the delivery device and a location within the holder shaft 529. The central shaft 527 may provide a fixed connection between the distal tip of the delivery device and the holder shaft 529. The central shaft 527 may extend from the distal tip of the delivery device proximally to a location within the holder shaft 529 adjacent the holder 534, or may extend all the way to the proximal end of the delivery device. The central shaft 527 may have a lumen for a guide wire (not shown) therethrough. As with the retainer 230 described above, a user may load a valve 506 in the compartment 523 by capturing the V-shaped junctions of the stent portion of the valve between the recesses of the pusher 532 and the ribs of the holder 534 by sliding the holder proximally towards the pusher.

With the proximal end of the stent portion of the valve 506 captured between the pusher 532 and the holder 534, the user may move a locking pin 519 positioned in the hub 520 to a locked position. In the locked position, the locking pin 519 temporarily affixes the inner shaft 526 to the holder shaft 529 to fix the relative positions of the pusher 532 and the holder 534. To deploy the valve 506, the user may first withdraw the distal sheath 524 from around the compartment 523 by sliding the hub 521 proximally. Subsequently, the user may move the locking pin 519 to an unlocked position and slide the holder shaft 529 distally, and with it the holder 534, to unclamp the valve 506 from the retainer 530 so that the valve can self-expand and thereby become released from the retainer.

FIG. 9 shows another exemplary transfemoral delivery device 610 for a collapsible prosthetic heart valve according to the invention. The structure and function of the delivery device 610 is similar to the structure and function of the delivery device 510 described above in all respects, except that the pusher 632 is longitudinally slidable relative to the holder 634 to allow a user to capture the stent portion of a prosthetic valve in the retainer 630, rather than having the holder slidable relative to the pusher. Whether the pusher, the holder, or both components are configured to be slidable or fixed in a given embodiment may depend on how the respective hubs are attached to an operating handle (not shown). The stent portion of a prosthetic valve may be captured between the pusher and holder in a similar manner regardless of whether the pusher, the holder, or both components are configured to be slidable.

Figure 10A:
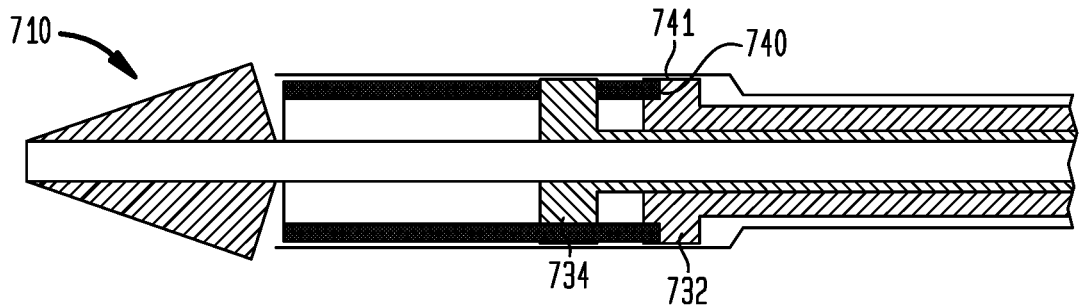
FIG. 10A is a longitudinal cross-section of the distal portion of a transfemoral delivery device for a collapsible prosthetic heart valve including a pusher portion having a single circumferential recess.
Figure 10B:
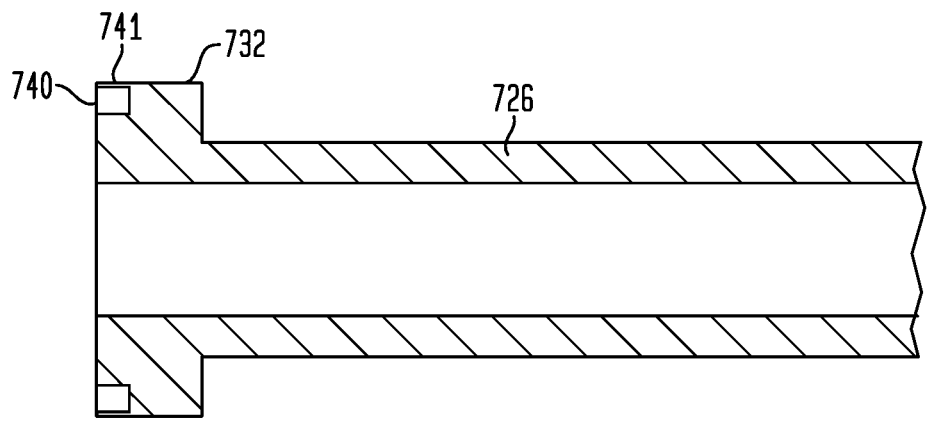
FIG. 10B is an enlarged longitudinal cross-section of the pusher portion shown in FIG. 10A.

Referring now to FIGS. 10A and 10B, yet another exemplary transfemoral delivery device 710 for a collapsible prosthetic heart valve according to the invention is shown. The delivery device 710 is similar to the delivery devices 510 and 610 described above with reference to FIGS. 8 and 9, respectively, except that, rather than a plurality of discrete recesses, the pusher 732 includes a single recess 740 having an annular wall 741 extending continuously around the entire circumference thereof. When a valve is assembled in the delivery device 710, the V-shaped junctions of the stent portion of the valve may be retained by the annular wall 741 such that the V-shaped junctions do not splay radially outward. The presence of the annular wall 741 in the pusher 732 may make it easier for the pusher 732 to retain the proximal end of a valve during loading of the valve into the delivery device 710. The pusher 732, the holder 734, or both components may be slidable or fixed relative to one another. Although the ribs in the holder 734 are not shown in FIG. 10A, the holder may have any of the rib configurations disclosed herein.

Figure 11:
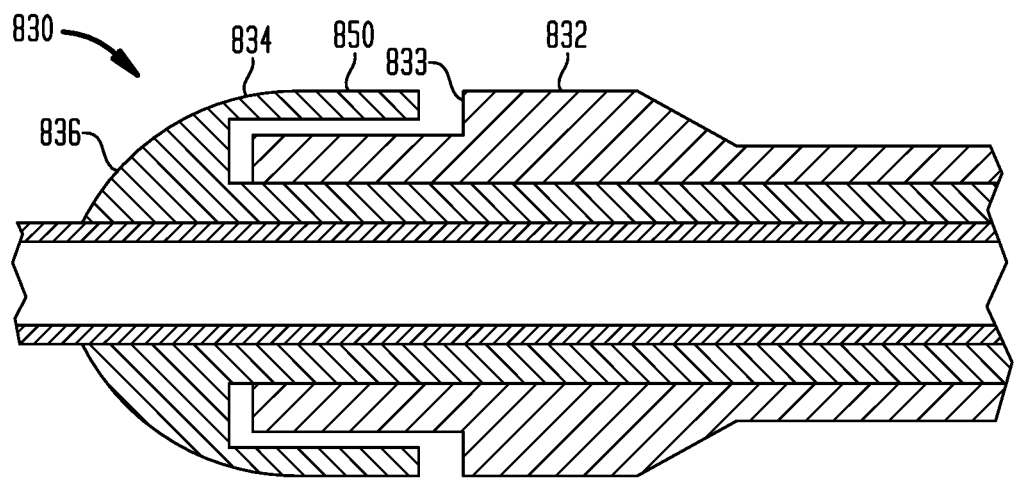
FIG. 11 is an enlarged longitudinal cross-section showing a retainer with a slidable portion suitable for use in the delivery device of FIGS. 8 and 9.

A retainer 830 in accordance with another embodiment of the invention is shown in FIG. 11. The retainer 830 is similar to the retainers 230, 530, 630, and 730 having a movable pusher and/or holder as described above, except that the ribs 850 extend proximally from a conical end 836 attached to the holder 834, rather than extending radially outward from an outer surface of the holder. Although the recesses in the pusher 832 are not visible in the particular cross-section shown in FIG. 11, the holder may have recesses extending proximally from the retention edge 833 that are adapted to receive V-shaped junctions of the stent portion of a collapsible prosthetic valve. The pusher 832, the holder 834, or both components may be slidable relative to one another or fixed.

Figure 12:
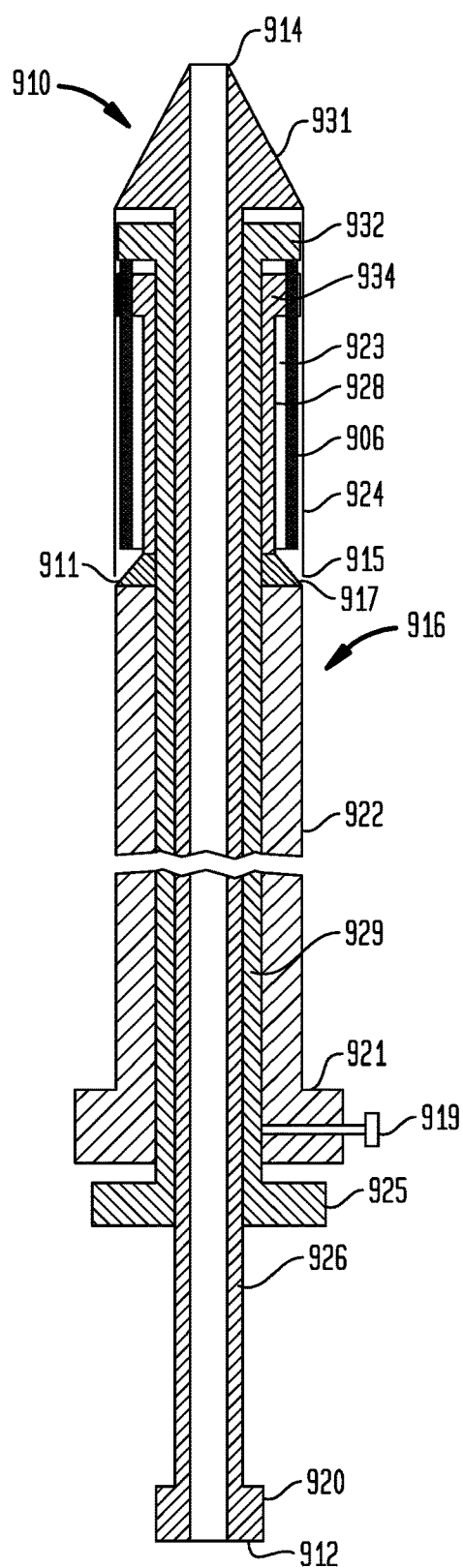
FIG. 12 is a longitudinal cross-section of a transapical delivery device for a collapsible prosthetic heart valve having a slidable portion.

Referring now to FIG. 12, an exemplary transapical delivery device 910 for a collapsible prosthetic heart valve 906 has a catheter assembly 916 for delivering the heart valve to and deploying the heart valve at a target location. The delivery device 910 extends from a proximal end 912 to a distal end 914. The catheter assembly 916 is adapted to receive a collapsible prosthetic heart valve in an assembled condition in a compartment 923 defined around a support shaft 928 and covered by a distal sheath 924.

The support shaft 928 extends from a holder 934 fixed at the distal end of the support shaft to a retainer 911 fixed at the proximal end of the support shaft. The retainer 911, in turn, is connected to an outer shaft 922 having a hub 921 on its proximal end. The holder 934 and a pusher 932 are adapted to hold a collapsible prosthetic valve in the compartment 923 defined around the support shaft 928. The pusher 932 may be affixed to a pusher shaft 929 that extends through the support shaft 928 and the outer shaft 922 to a hub 925. An inner shaft 926 may extend through the pusher shaft 929 from a hub 920 at its proximal end to a connection to an atraumatic tip 931 at the distal end 914 of the delivery device 910.

The distal sheath 924 surrounds compartment 923 and is slidable relative to the support shaft 928 such that it can selectively cover or uncover a collapsed prosthetic valve 906 positioned in the compartment. The distal sheath 924 is affixed at its distal end to the tip 931. The proximal end 915 of the distal sheath 924 may abut a conical surface 917 of the retainer 911 when the distal sheath fully covers the compartment 923, as shown in FIG. 12, and is spaced apart from the conical surface 917 when the compartment 923 is at least partially uncovered.

In the embodiment shown in FIG. 12, the pusher 932 and/or the holder 934 may slide relative to one another to capture the distal end of the stent portion of the valve 906 therebetween. Although the recesses in the pusher 932 and the ribs on the holder 934 are not shown in FIG. 12, the pusher and the holder may have any of the recess and rib configurations disclosed herein. As with the delivery devices 510 and 610 described above, a user may load a valve 906 in the compartment 923 by capturing the V-shaped junctions of the stent portion of the valve between the recesses of the pusher 932 and the ribs of the holder 934 by sliding the pusher and/or the holder longitudinally towards one another.

The delivery device 910 may include a locking pin 919 adapted, in a locked position, to temporarily affix the outer shaft 922 (and with it, the support shaft 928) to the pusher shaft 929 and thereby fix the relative positions of the pusher 932 and the holder 934. With the distal end of the stent portion of the valve 906 captured between the pusher and the holder, the user may move the locking pin 919 to a locked position to fix the relative positions of the pusher and the holder.

To deploy the valve 906, the user may first withdraw the distal sheath 924 from around the compartment 923 by sliding the inner shaft 926 distally relative to the outer shaft 922 and the pusher shaft 929. Subsequently, the user may move the locking pin 919 to an unlocked position, and may slide the pusher 932 and the holder 934 longitudinally away from one another to unclamp the valve 906 from within the retainer 930 so that the valve can self-expand and thereby become released from the delivery device 910.

Figure 13:
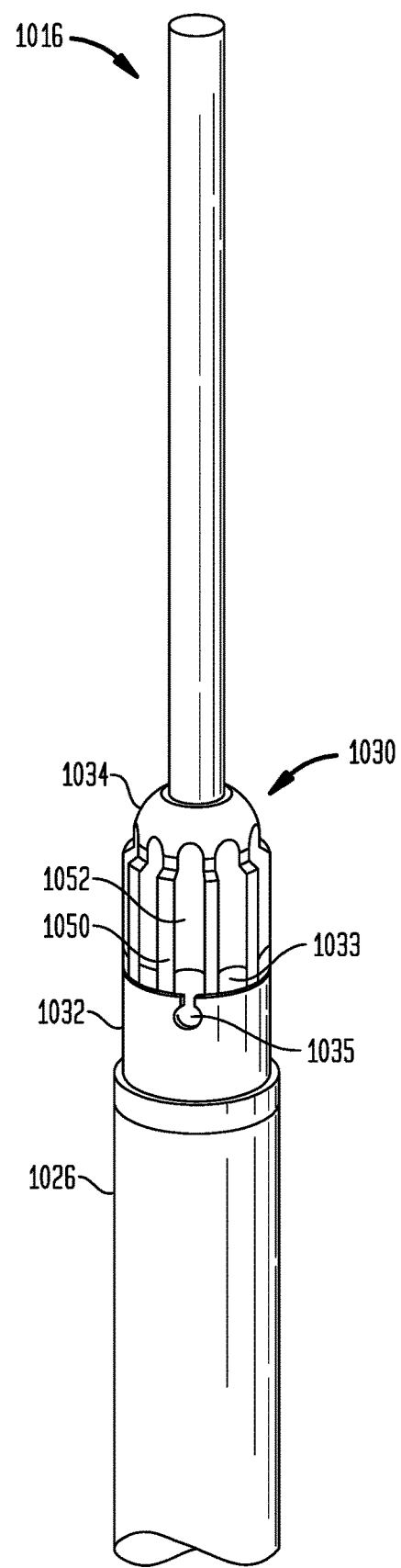
FIG. 13 is a perspective view of a retainer suitable for use in a transfemoral or transapical delivery device for a conventional collapsible heart valve having retention members.

Referring now to FIG. 13, a retainer 1030 in accordance with another embodiment of the invention is shown. The retainer 1030 is adapted to retain and align the stent portion of a conventional prosthetic valve, such as the stent portion 6 shown in FIG. 1. The retainer 1030 may be incorporated either in a transfemoral delivery device, such as the delivery device 10 described above, with the valve extending distally from the retainer, or in a transapical delivery device, such as the delivery device 910 described above, with the valve extending proximally from the retainer.

The retainer 1030 includes a retention portion 1032 affixed to an inner shaft 1026, the retention portion including a plurality of acceptances 1035 adapted to receive retention members of a conventional valve, such as the retention members 7 shown in FIG. 1. The retainer 1030 also includes a spacer portion 1034 affixed to the retention portion 1032, the spacer portion including a plurality of ribs 1050 extending in a longitudinal direction, each adjacent pair of ribs defining a channel 1052 therebetween. The ribs 1050 preferably are spaced uniformly in a circumferential direction around the spacer portion 1034.

To load the stent portion of a conventional prosthetic valve into the retainer 1030 for delivery into a patient, a user may insert the retention members of the valve into the acceptances 1035, and the V-shaped junctions at the aortic end of the stent into respective channels 1052. The channels 1052 that are longitudinally aligned with an acceptance 1035 can receive the V-shaped junction aligned in the longitudinal direction with a retention member.

In a conventional delivery system, the stent portion of a conventional prosthetic valve can become twisted during delivery of the valve to a desired location in a patient, and the stent struts can bind against the distal sheath covering the valve, potentially deforming or damaging the struts and/or increasing the force required to unsheathe the valve. Compared to a conventional retainer, the retainer 1030 can keep the V-shaped junctions of the stent struts aligned during delivery of the valve within a patient, thereby preventing damage to the valve and minimizing the force needed for unsheathing and deployment.

Although the various retainer embodiments have been described here in connection with retaining for deployment a prosthetic valve having a collapsible stent structure, all of the retainer embodiments may be used for other purposes. In particular, the various embodiments of retainers may be used to retain conventional collapsible stents that do not contain a valve structure.

Although the invention herein has been described with reference to particular embodiments in which the annulus end of a prosthetic valve is deployed first, it is to be understood that the invention contemplates embodiments in which the aortic end of a valve is deployed first. In such embodiments (not shown), the annulus end of the stent portion of the valve may be engaged with a retainer, while the aortic end of the stent may be remote from the retainer and may be unsheathed first.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present invention enjoys wide industrial applicability including, but not limited to, delivery devices for collapsible prosthetic heart valves and methods of delivering collapsible prosthetic heart valves.

The inventino claimed is:

1. A delivery device for a collapsible prosthetic heart valve, the delivery device comprising:
   a catheter assembly including a principal shaft around which a compartment is defined, the compartment being adapted to receive the valve in an assembled condition, the catheter assembly further including a distal sheath adapted to selectively cover and uncover the compartment and the valve, the distal sheath extending around the principal shaft at least when the distal sheath covers the compartment; and
   a retainer, including:
      a retention portion fixedly connected to the principal shaft and including a plurality of circumferentially spaced acceptances each having a closed end and an open end spaced apart from the closed end by a first distance in a longitudinal direction of the catheter assembly; and
      a spacer portion fixedly connected to the principal shaft and having a plurality of circumferentially spaced elongated ribs connected to and extending from an end of the retention portion in the longitudinal direction, each adjacent pair of elongated ribs defining a channel therebetween, the channels including:
         a first group and second group that together comprise all of the channels, the first group containing a first positive number of the channels and the second group containing a remaining positive number of the channels that is not in the first group,
         the first group of the channels each having an open end and a closed end spaced apart from one another by a second distance in the longitudinal direction that is greater than the first distance,
         the second group of the channels each having a first open end and a second open end spaced apart from one another in the longitudinal direction by the second distance, the second open end of each of the second channels being the open end of a corresponding one of the acceptances,
         the first open end of each of the second channels being spaced apart from the closed end of the corresponding one of the acceptances by a third distance in the longitudinal direction that is greater than the first distance and greater than the second distance.

2. The delivery device of claim 1, wherein the acceptances are configured to receive corresponding retention members of the collapsible prosthetic heart valve therein, the acceptances and the retention members being equal in number.

3. The delivery device of claim 1, wherein the principal shaft is elongated in the longitudinal direction, and the elongated ribs each extend in the longitudinal direction.

4. The delivery device of claim 1, wherein the principal shaft is elongated along a longitudinal axis, and the elongated ribs are spaced uniformly about the longitudinal axis in a circumferential direction around the spacer portion.

5. The delivery device of claim 1, wherein each acceptance is aligned in the longitudinal direction with a corresponding one of the channels.

6. A delivery device, comprising:
a collapsible prosthetic heart valve having a stent portion including a plurality of junctions defining an end of the stent portion and a plurality of cell openings defined therein, and retention members extending from some of the junctions past the end of the stent portion of the valve;
a catheter assembly including a principal shaft around which a compartment is defined, the collapsible prosthetic heart valve positioned in the compartment in an assembled condition, the catheter assembly further including a distal sheath adapted to selectively cover and uncover the compartment and the valve, the distal sheath extending around the principal shaft at least when the distal sheath covers the compartment; and
a retainer, including:
a retention portion fixedly connected to the principal shaft and including a plurality of circumferentially spaced acceptances each having a closed end and an open end spaced apart from the closed end by a first distance in a longitudinal direction of the catheter assembly, each retention member positioned in a corresponding one of the acceptances; and
a spacer portion fixedly connected to the principal shaft and having a plurality of circumferentially spaced elongated ribs connected to and extending from an end of the retention portion in the longitudinal direction, each adjacent pair of elongated ribs defining a channel therebetween, the channels including:
a first group and second group that together comprise all of the channels, the first group containing a first positive number of the channels and the second group containing a remaining positive number of the channels that is not in the first group,
the first group of the channels each having an open end and a closed end spaced apart from one another by a second distance in the longitudinal direction that is greater than the first distance,
the second group of the channels each having a first open end and a second open end spaced apart from one another in the longitudinal direction by the second distance, the second open end of each of the second channels being the open end of a corresponding one of the acceptances,
the first open end of each of the second channels being spaced apart from the closed end of the corresponding one of the acceptances by a third distance in the longitudinal direction that is greater than the first distance and greater than the second distance.

7. The delivery device of claim 6, wherein the acceptances and the retention members are equal in number.

8. The delivery device of claim 6, wherein the principal shaft is elongated in the longitudinal direction, and the elongated ribs each extend in the longitudinal direction.

9. The delivery device of claim 6, wherein the principal shaft is elongated along a longitudinal axis, and the elongated ribs are spaced uniformly about the longitudinal axis in a circumferential direction around the spacer portion.

10. The delivery device of claim 6, wherein each junction is V-shaped.

11. The delivery device of claim 6, wherein each acceptance is aligned in the longitudinal direction with a corresponding one of the channels.

12. The delivery device of claim 6, wherein each junction at the end of the stent portion of the valve is separated from other ones of the junctions by the elongated ribs.

13. A method of delivering a collapsible prosthetic heart valve, the method comprising:
providing a delivery device including a principal shaft around which a compartment is defined, the principal shaft extending along a longitudinal axis of the delivery device extending in a longitudinal direction, a distal sheath adapted to selectively cover and uncover the compartment, the distal sheath extending around the principal shaft at least when the distal sheath covers the compartment, and a retainer including a retention portion and a spacer portion, the retention portion fixedly connected to the principal shaft and including a plurality of circumferentially spaced acceptances each having a closed end and an open end spaced apart from the closed end by a first distance in a longitudinal direction of the catheter assembly, and the spacer portion fixedly connected to the principal shaft and having a plurality of circumferentially spaced elongated ribs connected to and extending from an end of the retention portion, each adjacent pair of elongated ribs defining a channel therebetween, the channels including:
a first group and second group that together comprise all of the channels, the first group containing a first positive number of the channels and the second group containing a remaining positive number of the channels that is not in the first group,
the first group of the channels each having an open end and a closed end spaced apart from one another by a second distance in the longitudinal direction that is greater than the first distance,
the second group of the channels each having a first open end and a second open end spaced apart from one another in the longitudinal direction by the second distance, the second open end of each of the second channels being the open end of a corresponding one of the acceptances,
the first open end of each of the second channels being spaced apart from the closed end of the corresponding one of the acceptances by a third distance in the longitudinal direction that is greater than the first distance and greater than the second distance;
mounting in the compartment the collapsible prosthetic heart valve having a stent portion including a plurality of junctions defining an end of the stent portion and a plurality of cell openings defined therein, and retention members extending from some of the junctions past the end of the stent portion of the valve, the valve being mounted so that each retention member is positioned in a corresponding one of the acceptances, and each junction is positioned in a corresponding one of the channels;

moving the distal sheath to cover the compartment and the valve;

inserting the delivery device in a patient to position the valve at a target location; and deploying the valve by moving the distal sheath to uncover the compartment and the valve.

14. The method of claim 13, wherein the principal shaft is elongated in the longitudinal direction, and the elongated ribs each extend in the longitudinal direction.

15. The method of claim 13, wherein the principal shaft is elongated along a longitudinal axis, and the elongated ribs are spaced uniformly about the longitudinal axis in a circumferential direction around the spacer portion.

16. The method of claim 13, wherein each acceptance is aligned in the longitudinal direction with a corresponding one of the channels.

17. The method of claim 13, wherein during the mounting step, each junction at the end of the stent portion of the valve is separated from other ones of the junctions by the elongated ribs.

18. The method of claim 13, wherein the mounting step includes mounting the valve such that the valve extends distally from the retainer, and the inserting step includes inserting the delivery device into the femoral artery of the patient.

19. The method of claim 13, wherein the mounting step includes mounting the valve such that the valve extends proximally from the retainer, and the inserting step includes inserting the delivery device into the apex of the heart of the patient.

* * * * *